United States Patent [19]

Wissner et al.

[11] Patent Number: 4,883,816
[45] Date of Patent: Nov. 28, 1989

[54] ANTIHYPERTENSIVE DERIVATIVES

[75] Inventors: Allan Wissner, Ardsley; Phaik E. Sum, New City, both of N.Y.; Robert E. Schaub, Upper Saddle River, N.J.

[73] Assignee: American Cyanamid Company, Stamford, Conn.

[21] Appl. No.: 157,055

[22] Filed: Feb. 16, 1988

Related U.S. Application Data

[62] Division of Ser. No. 679,788, Dec. 10, 1984, Pat. No. 4,762,942.

[51] Int. Cl.$^4$ .................. A61K 31/10; C07C 147/00
[52] U.S. Cl. ................................. 514/546; 560/256
[58] Field of Search ......................... 514/546; 560/256

*Primary Examiner*—Anton H. Sutto
*Attorney, Agent, or Firm*—R. P. Raymond

[57] ABSTRACT

Antihypertensive sulfonyl derivatives having the following formula are described:

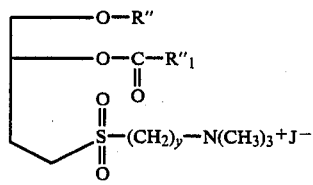

where
R″ is a $C_2$–$C_{20}$ alkyl group,
R″$_1$ is a $C_1$ to $C_4$ alkyl group,
y is an integer from 2 to 10 and
J$-$ is a pharmocologically acceptable anion.

6 Claims, No Drawings

ANTIHYPERTENSIVE DERIVATIVES

This is a divisional of application Ser. No. 679,788, filed Dec. 10, 1984, now U.S. Pat. No. 4,762,942.

BACKGROUND OF INVENTION

This invention pertains to novel phosphate derivatives, and to methods of preparation of such compounds. This invention is also concerned with compositions useful in the treatment of hypertension.

It is estimated that approximately fifteen percent (15%) or more of the adult population in the United States is hypertensive, i.e., having blood pressures greater than or equal to about 160/95 mm Hg. Of that population, approximately one-half is unaware of their hypertensive condition. An untreated hypertensive is at great risk of developing disabling or fatal left ventricular failure, myocardial infarction, cerebral hemorrhage or infarction, and renal failure at an early age. Hypertension is generally considered the most important risk factor predisposing to coronary and cerebral atherosclerosis. However, it is believed that effective medical control of hypertension will prevent or forestall all complications associated with hypertension, and will prolong the life of the hypertensive patient.

Drug therapy for hypertension includes use of diuretics, sympathetic depressants (e.g., α-blockers such as reserpine), vasodilators and finally blockers of sympathetic transmission at the neuroeffector junction (e.g., guanethidine or clonidine).

Among the vasodilators currently employed in hypertension therapy are diazoxide and sodium nitroprusside. Side effects of diazoxide therapy include nausea, vomiting, hyperglycemia and tachycardia. Side effects from sodium nitroprusside therapy include nausea, vomiting, agitation, muscular twitching and cutis anserina if blood pressure is reduced too rapidly. Minoxidil is also often used as a vasodilator in hypertension therapy. However, the side effects of minoxidil include sodium and water retention, and hirsutism. Hydralazine, a mild vasodilator, is also employed. Its side effects include headaches, tachycardia, fluid retention, aggravation of angina, gastrointestinal irritation, lupus-like syndrome, drug fever and psychosis.

Acetyl glyceryl ether phosphocholines have been recognized as having potent biological activity in platelet activation, and in vasoconstriction and vasodilation. See, e.g., U.S. Pat. No. 4,329,302, which issued on May 11, 1982 to Hanahan et al. Such phosphocholines have been identified as both a platelet activation factor (PAF) and an antihypertensive polar renomedullary lipid (APRL). See R. L. Wykle et al., FEBS LETTERS, 141: 29-32 (1982); M. L. Blank et al., BIOCHEMICAL AND BIOPHYSICAL RESEARCH COMMUNICATIONS, 90: 1194-1200 (1979). Antihypertensive phosphocholines do not occur as pre-formed components in the body; rather, such phosphocholines are synthesized by certain cells. See J. Benveniste et al., INT. ARCHS. ALLERGY APPL. IMMUNN., 66 (Supp. 1): 121-126 (1981); E. E. Muirhead, HYPERTENSION, 2: 444-464 (1980). APRL has been described as being accountable in great measure for the endocrine-type antihypertensive action exerted by the renal medullary and the renomedullary interstitial cells. M. L. Blank et al., ID.

BRIEF SUMMARY OF THE INVENTION

The phosphate derivatives of the present invention have the formula:

Formula 1

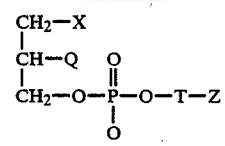

wherein X is selected from one or more of: (a) $C_1$-$C_{24}$ branched or straight chain alkyl; (b) $C_1$-$C_{24}$ branched or straight chain alkoxy; (c)

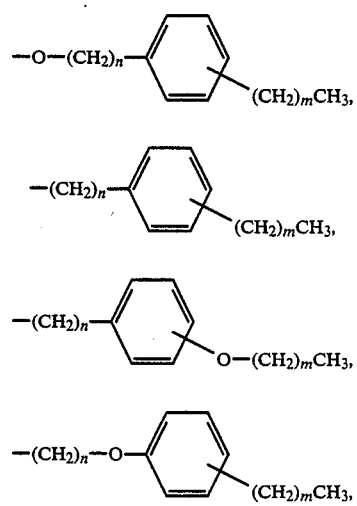

wherein n and m are integers from zero to 25 and the sum of n and m is less than or equal to 25; (d) phenyl; (e) substituted phenyl, wherein the substituents are selected form one or more of $C_1$-$C_{20}$ branched or straight chain alkyl, $C_1$-$C_{20}$ branched or straight chain alkoxy, halogen, trifluoromethyl, phenyl and substituted phenyl; (f) phenoxy, and (g) substituted phenoxy, wherein the substituents are selected from one or more of the group consisting of $C_1$-$C_{20}$ branched or straight chain alkyl, halogen, trifluoromethyl, phenyl and substituted phenyl; Q is selected from the group consisting of:

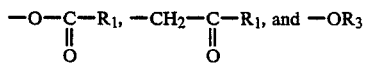

wherein $R_1$ is selected from the group consisting of hydrogen, $C_1$-$C_4$ branched or straight chain alkyl, $C_1$-$C_4$ branched or straight chain alkoxy and $C_1$-$C_4$ branched or straight chain alkylamino and $R_3$ is $C_1$-$C_4$ alkyl, with the proviso that when Q is

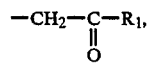

$R_1$ is $C_1$-$C_4$ branched or straight chain alkyl; wherein T is a bivalent radical selected from the group consisting of —(CHR)$_p$— and

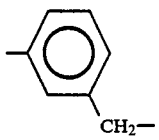

wherein p is an integer from 1 to 15, the moiety —(CHR)$_p$— represents an alkylene chain substituted at any position with one or more $C_1$-$C_{10}$ alkyl groups or phenyl groups, and the moiety

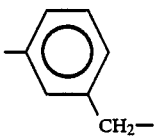

is bound with the oxygen atom attached directly to the aromatic ring; and wherein Z is selected from the group consisting of $N^+(R_2)_3$ and

wherein $R_2$ may be the same or different and is selected from the group consisting of hydrogen and $C_1$-$C_4$ branched or straight chain alkyl and q is an integer from 4 to 7.

Such derivatives may be in racemic form or as the individual R and S enantiomers.

According to the sequence of reactions outlined in Flowsheet A a hydroxymethyl ketone 2 is treated with an excess of reagents 3a or 3b in an inert solvent such as carbon tetrachloride in the presence of at least one equivalent of an amine base such as triethylamine giving, after hydrolysis in a buffer such as aqueous sodium acetate, the compounds of formula 4.

Compound 4 can readily be reduced to alcohol 5 using sodium borohydride in an alcohol solvent such as ethanol or 1-butanol. Nucleophilic displacement of the bromine atom of 5 to give the compound 7 is accomplished by treatment of 5 with an excess of an amine such as 6a or 6b, either in an inert solvent such as acetonitrile, tetrahydrofuran or chloroform at elevated temperatures (about 50°–150° C.) in an enclosed vessel or by heating at about 60°–70° C. a solution of 6 and the amine in a mixture of chloroform, 1-propanol, dimethylformamide and water (about 3:5:5) or other inert solvent mixture. When the compounds represented by structures 6a and 6b are tertiary amines, the products 7 of this reaction are quaternary ammonium salts; in these cases it may be desirable to prepare the internal salt by treatment of an aqueous-alcohol solution of the compound with a suspension of silver carbonate. The compounds represented by formula 7 can be converted to compounds 1 of this invention wherein $R_1$ is a $C_1$-$C_4$ alkyl group by the reaction of 7 with an anhydride 8 in the presence of a base catalyst such as triethylamine in an inert solvent such as chloroform.

The compounds represented by the formula 7 can be converted to the compounds 1 of this invention wherein $R_1$ is a $C_1$-$C_4$ alkoxy group by the reaction of 7 with a pyrocarbonate 10 in the absence of solvent at elevated temperature (about 50°–150° C.).

The compounds represented by the formula 7 can be converted to the compounds of 1 of this invention wherein $R_1$ is hydrogen by the reaction of 7 with 97% formic acid at room temperature for about 3 to 7 days.

The compounds represented by the formula 7 can be converted to the compounds 1 of this invention wherein $R_1$ is a $C_1$-$C_4$ alkylamino group by treatment of 7 with an isocyanate 9 in an inert solvent such as toluene at about 25°–100° C. for about 1 to 7 days.

The preparation of the hydroxmethyl ketone precursors of formula 2 are described in a co-pending application (Ser. No. 457,097, filed Jan. 10, 1983), which is incorporated herein by reference and in the prior art.

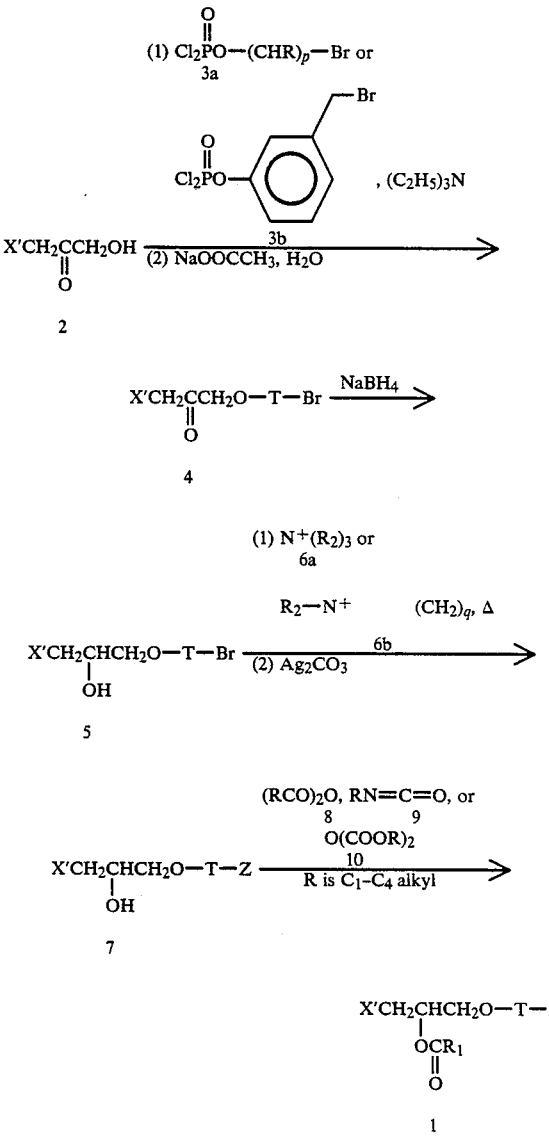

The preparation of the compounds of this invention encompassed by formula 11 is described hereinbelow in Flowsheet B, wherein $R_4$ is a $C_1$-$C_{24}$ branched or straight chain alkyl group or

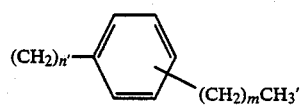

FLOWSHEET B

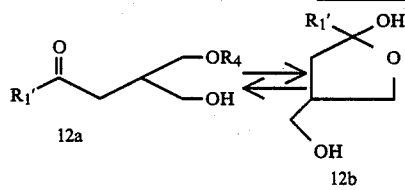

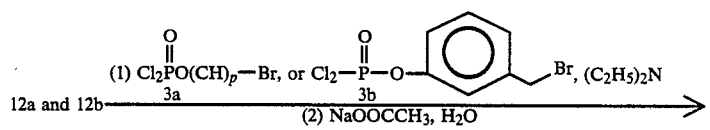

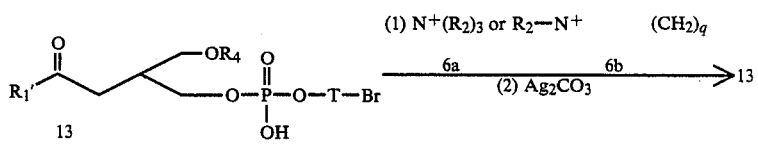

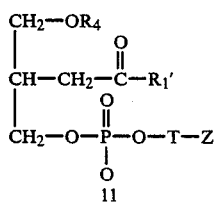

wherein n' and m are integers from zero to 25 and the sum of n' and m is equal to, or less than 25 and n' must be greater than zero; $R_1$ is a $C_1$–$C_4$ alkyl group; q, p, Z, T, and $R_2$ are defined as given hereinabove.

The reaction of an equilibrium mixture of 12a and 12b with either reagents 3a or 3b as described hereinabove gives, after hydrolysis in a buffer such as sodium acetate solution, the compound 13. The reaction of 13 with the amines 6a or 6b as described above furnishes the compounds of this invention represented by formula 11. As described above, compound 11 can be converted to the corresponding internal salt by treatment with silver carbonate.

The precursor compounds represented by formula 12a and 12b are described in a co-pending application (Ser. No. 457,097, filed Jan. 10, 1983).

The preparation of compounds of this invention encompassed by formula 14 is described hereinbelow in Flowsheet C, wherein X', $R_1'$, T, p, Z, q, and $R_2$ are defined hereinabove. A mixture of the keto 15a and hemiketal 15b isomers react with either reagents 3a or 3b as described hereinabove to furnish 16 after hydrolysis in a buffer such as sodium acetate solution. The reaction of 16 with the amines 6a or 6b as described above furnishes the compounds of this invention represented by formula 14. As described above, compound 14 can be converted to the corresponding internal salt by treatment with silver carbonate.

The precursor compounds 15a and 15b are described in a co-pending application (Ser. No. 457,097, filed Jan. 10, 1983).

FLOWSHEET C

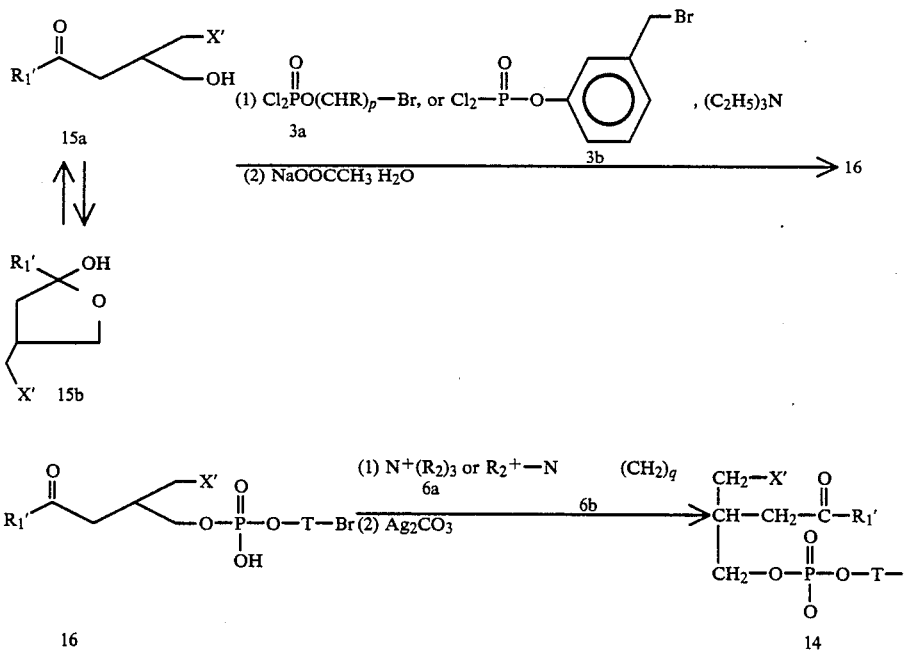

The compounds of this invention encompassed by formula 17 are prepared as described hereinbelow in Flowsheet D wherein q, p, $R_2$, $R_1$ and Z are as defined above. T' is a bivalent radical of the formula —(CHR'-)$_p$— which represents an alkylene chain substituted at any position with one or more $C_1$-$C_{10}$ alkyl groups or phenyl groups with the proviso that the carbon atom substituted with the amine group cannot be substituted with a phenyl group. $R_5$ is selected from the group consisting of $C_1$-$C_{24}$ branched or straight chain alkyl,

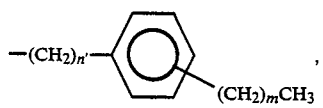

phenyl, or substituted phenyl wherein the substituents are selected from one or more of the group consisting of $C_1$-$C_{20}$ branched or straight chain alkyl, halogen, trifluoromethyl, phenyl, and substituted phenyl.

Treatment of 18 with reagent 19 as described hereinabove, furnishes, after hydrolysis with a sodium acetate buffer, the compound 20. The reaction of 20 with amines 6a or 6b as described above gives the compound 21.

When the compound represented by structures 6a or 6b are tertiary amines, the products of (21) of this reaction are quaternary ammonium salts; in these cases it may be desirable to prepare the internal salt by treatment of an aqueous-alcohol solution of the compound with a suspension of silver carbonate. The benzyl protecting group of 21 can be removed by catalytic hydrogenation using a catalyst such as palladium on carbon (5%) to give the alcohol 22.

The compounds represented by the formula 22 can be converted to compounds 17 of this invention wherein $R_1$ is an alkyl group by the reaction of 22 with an anhydride 8 in the presence of a base catalyst such as triethylamine in an inert solvent such as chloroform.

The compounds represented by the formula 22 can be converted to compounds 17 of this invention wherein $R_1$ is a $C_1$-$C_4$ alkoxy group by the reaction of 22 with a pyrocarbonate 10 in the absence of solvent at elevated temperature (about 50°-150° C.).

The compounds represented by the formula 22 can be converted to compounds 17 of this invention wherein $R_1$ is hydrogen by the reaction of 22 with about 97% formic acid at room temperature for about 3 to 7 days.

The compounds represented by the formula 22 can be converted to compounds 17 of this invention wherein $R_1$ is a $C_1$-$C_4$ alkylamino group by treatment of 22 with an isocyanate 9 in an inert solvent such as toluene at about 25°-100° C. for about 1-7 days.

The precursor compounds of formula 18 are described in a co-pending application (Ser. No. 457,097, filed Jan. 10, 1983).

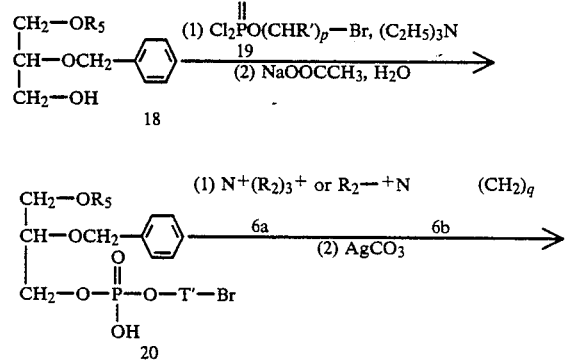

-continued
FLOWSHEET D

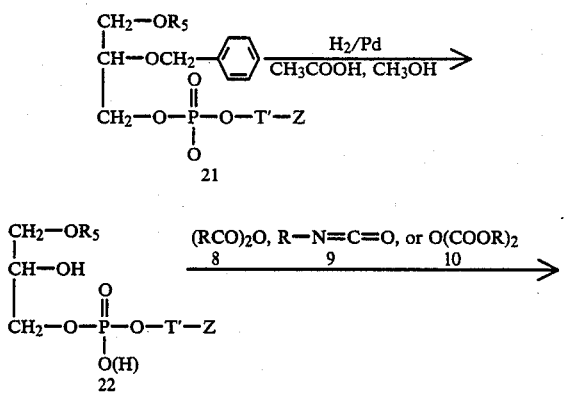

FLOWSHEET E

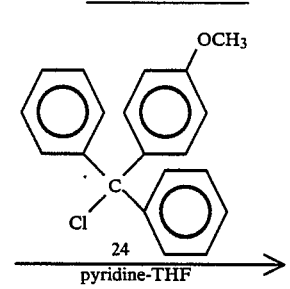

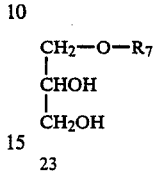

The compounds of this invention encompassed by formula 29 are prepared as outlined hereinbelow in Flowsheet E wherein, $R_1$, p, q, T, and Z are as defined above and $R_7$ is selected from the group consisting of $C_1$-$C_{24}$ branched or straight chain alkyl,

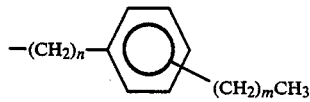

phenyl, or substituted phenyl wherein the substituents are selected from one or more of the group consisting of $C_1$-$C_{20}$ branched or straight chain alkyl, halogen trifluoromethyl, phenyl, and substituted phenyl.

Compound 23 is reacted with 24 in a mixture of pyridine and tetrahydrofuran or other inert solvent to give the compound 25 in which only the primary hydroxyl group has reacted. Acylation of 25 with an anhydride 8 using an amine base in an inert solvent gives 26. The alcohol protecting group of 26 can be removed without acyl migration by passing a solution of 26, in an inert solvent, through a column packed with a mixture of silicic acid and boric acid giving the alcohol 27. The reaction of 27 with reagents 3a or 3b in an inert solvent in the presence of an amine base gives, after hydrolysis in a buffer such as aqueous sodium acetate, the phosphate 28. The reaction of 28 with amines 6a or 6b as described above furnishes the compounds of this invention represented by formula 29. As described above, compound 29 can be converted to the corresponding internal salt by treatment with silver carbonate.

The preparation of the precursor diols of formula 23 are described in a co-pending application (Ser. No. 457,097, filed Jan. 10, 1983).

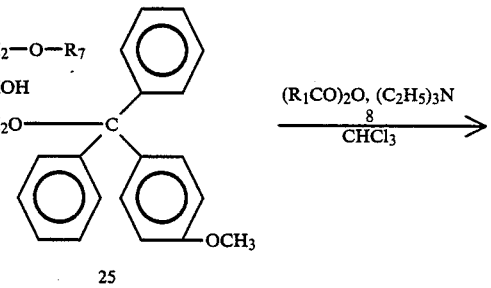

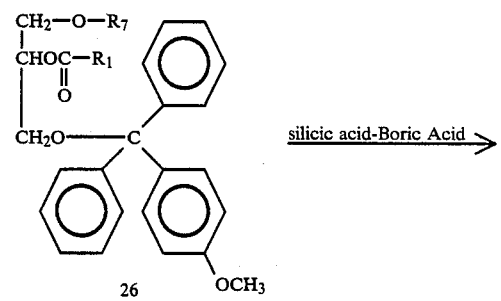

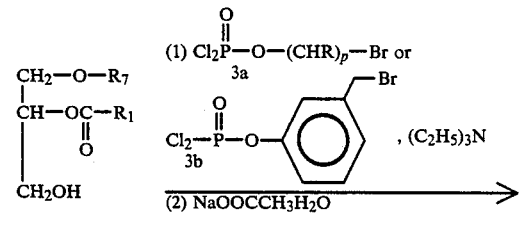

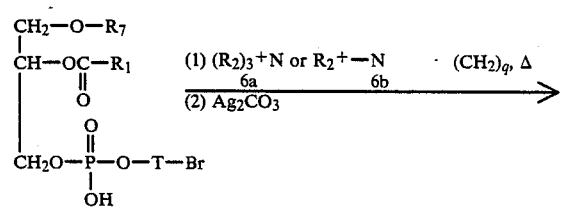

-continued
FLOWSHEET E

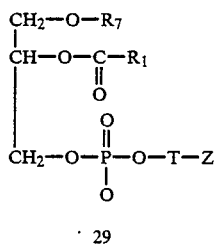

29

The preparation of compounds of this invention encompassed by formula 30 is described hereinbelow in Flowsheet F wherein $R_5$, p, q, T, and Z are as defined hereinabove and $R_3$ is a $C_1$-$C_4$ alkyl group.

The reaction of 31 with reagent 3a or 3b as described above gives compound 32. The reaction of 32 with alkyl amines 6a or 6b as described previously furnishes the compounds of this inventions represented by formula 30.

The precusors of formula 31 are described in a copending application (Ser. No. 457,097, Jan. 10, 1983).

FLOWSHEET F

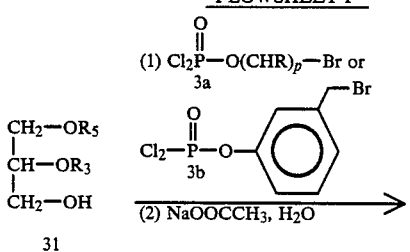

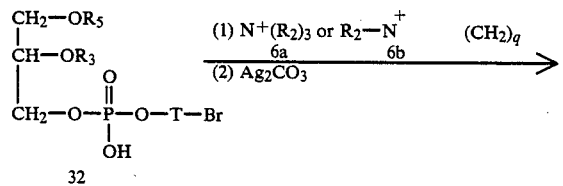

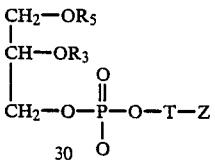

Methods by which the compounds of this invention can be prepared in their optically active forms are described in detail in a co-pending application (Ser. No. 457,097, filed Jan. 10, 1983) and in the prior art.

The reagents 3a and 3b needed to prepare the compounds of this invention are prepared as outlined in Flowsheet G wherein the moiety —(CHR)— is as defined hereinabove. The reaction of a bromoalcohol 33 or a bromophenol 34 with an excess of phosphorousoxychloride in an inert solvent such as carbon tetrachloride gives the reagents 3a or 3b, respectively. In some cases it is necessary to catalize this reaction by the addition of one equivalent of an amine base such as triethylamine.

The reagents 3a and 3b are useful for the preparation of the antihypertensive compounds of this invention.

FLOWSHEET G

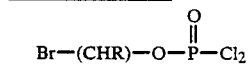

The compounds of the present invention are active as hypotensive agents as evidenced by their activity in the following test, the results of which are shown in Table I.

Under ether anesthesia, Weeks type cannulas (Peterson Technics) were surgically implanted in the abdominal aorta and vena cava of spontaneously hypertensive rats (Taconic Farms, Germantown, NY) and passed subcutaneously to the back of the neck where they were exteriorized. The cannulas were filled with saline, plugged and the rats returned to single cages where they were allowed food and water ad libitum.

At least three days following implantation of the cannulas, the rats were weighed and placed in Broome style restraining cages. The plug was removed from the aortic catheter which was connected to an arterial pressure transducer (Statham P23ID) using PE 100 polyethylene tubing and a stepdown connector fabricated from stainless steel hypodermic tubing. Mean arterial blood pressure was obtained by electrical damping of the pulse pressure channel. Heart rate was obtained from a tachograph triggered by the pulse pressure channel. All parameters were monitored on a Grass physiological recorder (Model 7).

The plug was removed from the vena cava catheter and a PE 20 polyethylene tubing extension was added using a piece of stainless steel hypodermic tubing. The other end was terminated with a 27G needle and one ml syringe.

All drugs were dissolved in saline or a mixture of ethanol and saline (25:75V:V) such that the volume injected intravenously was 0.1 ml/100 g body weight. All drugs were flushed in with 0.2 ml saline. Blood pressure was continually monitored both before and after introduction of the test compound.

TABLE I

| Compound | Dose (μg/kg) | No. of Rats | Peak Δ Mean Arterial Blood Pressure (mm,Hg) |
|---|---|---|---|
| 7-(acetyloxy)-4-hydroxy-N,N,N,2-tetramethyl-3,5,-9-trioxa-4-phosphapenta-cosan-1-aminium, 4-oxide, hydroxide, inner salt | 0.3 | 4 | −17.4 |
|  | 1.0 | 4 | −40.2 |
|  | 3.0 | 4 | −88.8 |
|  | 10.0 | 4 | −96.5 |
|  | 30.0 | 4 | −103.4 |
| 7-(acetyloxy)-4-hydroxy-N,N,N—trimethyl-1-phenyl-3,5,9-trioxa-4-phosphapenta-cosan-1-aminium, 4-oxide, hydroxide, inner salt | 10.0 | 1 | −59.0 |
| 3-[[[2-(acetyloxy)-3-(hexadecyloxy)-propoxy]- | 0.1 | 4 | −10.4 |
|  | 0.3 | 4 | −16.3 |

TABLE I-continued

| Compound | Dose (μg/kg) | No. of Rats | Peak Δ Mean Arterial Blood Pressure (mm,Hg) |
|---|---|---|---|
| hydroxyphosphinyl]oxy]- | 1 | 1.0 | −37.2 |
| N,N,N—trimethyl-benzene- | 3.0 | 4 | −83.9 |
| methanaminium, hydroxide inner salt | 10.0 | 4 | −91.0 |
| 8-(acetyloxy)-5-hydroxy- | 0.03 | 4 | −16.4 |
| N,N,N—trimethyl-4,6,10- | 0.10 | 4 | −36.3 |
| trioxa-5-phosphahexacosan- | 0.30 | 4 | −58.6 |
| 2-aminium, 5-oxide, | 1.0 | 4 | −103.1 |
| hydroxide, inner salt | 3.0 | 4 | −118.3 |
| 7-hydroxy-N,N,N—trimethyl- | 0.03 | 4 | −9.8 |
| 2-oxo-4-[(3-tetradecyl- | 0.10 | 4 | −17.6 |
| phenoxy)methyl]-3,6,8- | 0.30 | 4 | −78.7 |
| trioxa-7-phosphaundecan- | 1.0 | 4 | −95.9 |
| 10-aminium, 7-oxide, hydroxide inner salt | | | |

When the compounds are employed for the above utility, they may be combined with one or more pharmaceutically acceptable carriers, e.g., solvents, diluents and the like, and may be administered orally in such forms as tablets, capsules, dispersible powders, granules, or suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 0.05% up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 1.0 μg to about 100 mg/kg of animal body weight, preferably given in divided doses two to four times a day, or in sustained release form. For most large mammals the total daily dosage is from about 500 μg to about 5,000 mg preferably from about 350 μg to 3,500 mg. Dosage forms suitable for internal use comprise from about 25 μg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT and BHA.

The preferred pharmaceutical compositions from the stand-point of ease of preparation and administration are solid composition, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations should contain a preservative to prevent the growth of microorganisms.

The pharmaceutical forms suitable for injection use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

In addition to the above utility, some of the compounds of this invention (such as 23 of flowsheet E) are useful for the preparation of other compounds of this invention.

The invention will be more fully described in conjunction with the following specific examples which are not to be construed as limiting the scope of the invention.

EXAMPLE 1

1-Bromo-2-propanol

To an ice-cold slurry of 7.79 g of lithium aluminum hydride in 160 ml of ether, under an argon atmosphere, was added dropwise 79 g of 1-bromo-2-propanone in 25 ml of ether, maintaining the temperature at 5°–10° C. After the addition (1.5 hours) the mixture was stirred for 15 minutes at 30° C. Water was added dropwise, then 4N sulfuric acid. The ether layer was decanted and saved. The aqueous layer was extracted with three 100 ml portions of ether. The ether layers were combined, dried, filtered and evaporated on a steam bath. The residue was refrigerated overnight, then distilled at 46° C., 10 mm giving 21 g of the desired compound as an orange red oil.

EXAMPLE 2

Phosphorodichloridic acid 2-bromo-1-methylethyl ester

To a solution of 46 g of phosphorous oxychloride in 110 ml of carbon tetrachloride was added with stirring 21 g of 1-bromo-2-propanol. The mixture was stirred overnight, the solvent removed and the residue evaporated twice from toluene at 35° C., then evaporated to dryness giving a dark oil. This oil was distilled on a Kugelrohr at 75° C., 0.3 mm giving 16.3 g of the desired compound as a white oil.

EXAMPLE 3

2-Bromo-1-propanol

To 12.31 g of lithium aluminum hydride was added 700 ml of ether. This mixture was stirred at reflux for 3 hours, then cooled in an ice bath to 3° C. A 100 g portion of α-bromopropionyl bromide was added dropwise over 1.25 hours. This mixture was stirred for 2 hours at 0° C., then 35 ml of water was added dropwise followed by 225 ml of 4N sulfuric acid. The ether layer was separated and saved. The aqueous layer was extracted twice with ether. The ether solutions were combined, dried, filtered and concentrated to a yellow oil. This oil was distilled, 47°-48° C., 10 mm giving 48 g of the desired compound as a white oil.

EXAMPLE 4

Phosphorodichloridic acid-2-bromopropyl ester

To a solution of 42 g of phosphorous oxychloride in 110 ml of carbon tetrachloride was added dropwise with stirring a solution of 25 g of 2-bromo-1-propanol in 25 ml of carbon tetrachloride. This mixture was stirred overnight, then taken to dryness, evaporated twice from toluene and dried. The residue was distilled on a Kugelrohr 75° C., 0.05 mm, giving 26.1 g of the desired compound as a colorless oil.

EXAMPLE 5

Phosphorodichloridic acid-3-bromo-2,2-dimethylpropyl ester

To a solution of 18.35 g of phosphorous oxychloride in 55 ml of carbon tetrachloride was added dropwise a solution of 3-bromo-2,2-dimethyl-1-propanol in 20 ml of carbon tetrachloride. This mixture was stirred overnight, evaporated in vacuo, then evaporated twice from toluene at 35° C. and dried. The residue was distilled on a Kugelrohr 100° C., 0.3 mm giving the desired compound as a colorless oil.

EXAMPLE 6

2-Bromo-2-phenylethanol

To a stirred solution of 25 g of α-bromophenylacetic acid in 100 ml of dry tetrahydrofuran was added 151 ml of 1.0M diborane in tetrahydrofuran dropwise at 5° C. under argon over 30 minutes. This mixture was stirred overnight at room temperature, then cooled to 0° C. and 130 ml of tetrahydrofuran:water (1:1) was added dropwise. The mixture was then saturated with potassium carbonate and the tetrahydrofuran removed. The aqueous remainder was extracted three times with ether. The extracts were combined and dried. The residue was triturated with hexane and the solid collected giving the desired compound as white needles, mp 38°-39° C.

EXAMPLE 7

Phosphorodichloridic acid, 2-bromo-2-phenylethyl ester

To solution of 20 g of 2-bromo-2-phenylethanol in 75 ml of carbon tetrachloride was added 30 g of phosophorous oxychloride. This mixture was stirred on a water bath and 10 g of triethylamine in 40 ml of carbon tetrachloride was added dropwise over 30 minutes. This mixture was stirred at room temperature overnight, then filtered. The filtrate was taken to dryness, evaporated twice from toluene at 35° C. and then dried, giving 32.1 g of the desired compound as a yellow oil.

EXAMPLE 8

Phosphorodichloridic acid, 3-(bromomethyl)phenyl ester

To mixture of 17 g of m-bromomethylphenol in 150 ml of carbon tetrachloride under argon was added a solution of 25.5 g of phosphorous oxychloride in 25 ml of carbon tetrachloride. The solution was cooled in a water bath and a solution of 9.18 g of triethylamine in 35 ml of carbon tetrachloride was added dropwise with stirring over 40 minutes. This mixture was stirred in the water bath for 1 hour then overnight at room temperature, filtered through diatomaceous earth and washed with carbon tetrachloride. The mother liquor was taken to dryness giving 23 29 g of the desired compound as a pale yellow oil

EXAMPLE 9

2-Bromo-1-methylethylphosphoric acid 3-(hexadecyloxy)-2-(phenylmethoxy)propyl ester To a solution of 4.4 g of phosphorodichloridic acid 2-bromo-1-methylethyl ester in 140 ml of carbon tetrachloride, cooled in an ice bath under argon, was added dropwise with stirring 7.09 g of triethylamine. A solution of 5 g of 3-(hexadecyloxy)-2-(phenylmethoxy)-1-propanol in 15 ml of carbon tetrachloride was added dropwise. This mixture was stirred for 2 hours at room temperature then 100 ml of toluene was added and the mixture filtered through diatomaceous earth and washed with toluene. The mother liquor was taken to dryness. To the residue was added 110 ml of tetrahydrofuran and 110 ml of 0.5M aqueous sodium acetate. This mixture was stirred overnight under argon then the tetrahydrofuran was evaporated in vacuo. The remaining aqueous phase was acidified with 1N hydrochloric acid and extracted three times with ether. The ether extracts were combined, washed with saturated aqueous sodium chloride, dried and evaporated giving an oil. This oil was chromatographed on magnesium silcate as a chloroform solution, eluting with 10% methanol in chloroform and giving 6.58 g of the desired compound.

EXAMPLE 10

4-Hydroxy-N,N,N,2-tetramethyl-7-(phenylmethoxy)-3,5,9-trioxa-4-phosphapentacosan-1-aminium, 4-oxide, hydroxide, inner salt A solution of 6.49 g of 2-bromo-1methylethylphosphoric acid 3-(hexadecyloxy)-2-(phenylmethoxy)propyl ester in 125 ml of dry acetonitrile, 112 ml of dry chloroform and 50 ml of anhydrous trimethylamine was stirred in an oil bath at reflux temperature for 17 hours. The solvents were removed under reduced pressue and the residue dissolved in 65 ml of methanol. A 1.6 g portion of silver carbonate was added, the mixture sirred for 3 hours, filtered through diatomaceous earth and washed with methanol. The mother liquor was evaporated leaving a glass which was dissolved in 112 ml of chloroform, 125 ml of acetonitrile and 50 ml of trimethylamine were added and this mixture refluxed at 65° C. for 24 hours. This mixture was taken to dryness, the residue dissolved in 70 ml of methanol, 1.6 g of silver carbonate added and the mixture stirred under argon for 2 days. This mixture was filtered through diatomaceous earth, washed with methanol and the mother liquor evaporated giving an oil. This oil was dissolved in chloroform and chromatographed on silica gel, eluting with 10% methanol in chloroform, then 30% methanol in chloroform to remove higher Rf impurities and then eluting with methanol:chloroform:water (35:65:6). The product fractions were combined, taken to dryness and evaporated twice from toluene, giving 932 mg of the desired compound, mp 165°–170° C.

EXAMPLE 11

4-Hydroxy-N,N,N,2-tetramethyl-3,5,9-trioxa-4-phosphapentacosan-1-aminium,4-oxide, hydroxide, inner salt A solution of 1.6 g of 4-hydroxy-N,N,N,2-tetramethyl-7-(phenylmethoxy)-3,5,9-trioxa-4-phosphapentacosan-1-aminium, 4-oxide, hydroxide, inner salt in 35 ml of methanol and 35 ml of glacial acetic acid was hydrogenated with 600 mg of 5% palladium on carbon in a Parr apparatus at an initial pressure of 25 psi overnight. This mixture was filtered through diatomaceous earth, washed with methanol, the mother liquor taken to dryness and evaporated twice from toluene. The residual glass was triturated with 50 ml of ether, cooled in an ice bath and the solid collected and dried, giving 1.23 g of the desired compound as a white solid, mp 170° C.

EXAMPLE 12

7-(Acetyloxy)-4-hydroxy-N,N,N,2-tetramethyl-3,5,9-trioxa-4-phosphapentadosan-1-aminium, 4-oxide, hydroxide, inner salt A solution of 1.1 g of 4-hydroxy-N,N,N,2-tetramethyl-3,5,9-trioxa-4-phosphapentacosan-1-aminium, 4-oxide, hydroxide, inner salt, 5.24 ml of acetic anhydride, 3.09 ml of triethylamine and 55 ml of dry chloroform was stirred at reflux (70°–75° C.) for 5 hours and then taken to dryness. The residue was evaporated three times with toluene giving a glass. This glass was triturated with 50 ml of ether, then refrigerated and the solid collected, washed with ice cold ether and dried, giving 643 mg of the desired product as a white solid, mp 145° C.

EXAMPLE 13

3-(Hexadecyloxy)-2-(phenylmethoxy)phosphoric acid, 2-bromopropyl ester

To a solution of 4.4 g of phosphorodichloridic acid 2-bromopropyl ester in 140 ml of carbon tetrachloride, cooled in an ice bath under argon, was added with stirring 9.8 ml of triethylamine followed by the dropwise addition of a solution of 5 g of 3-(hexadecyloxy)-2-(phenylmethoxy)-1-propanol in 20 ml of carbon tetrachloride. The mixture was stirred in the ice bath for 30 minutes then at room temperature for 48 hours, 100 ml of toluene was added and the mixture was filtered through diatomaceous earth. The filtrate was evaporated and the residual gum stirred with 110 ml of tetrahydrofuran and 110 ml of 0.5M aqueous sodium acetate for 2 hours. The tetrahydrofuran was evaporated and the aqueous remainder acidified with 1N hydrochloric acid. This mixture was extracted three times with ether. The ether extracts were combined, washed with saturated aqueous sodium chloride, dried and evaporated to a syrup. This syrup was chromatographed on magnesium silicate, eluting with chloroform to remove the more mobile impurities then with 10% methanol in chloroform, giving 7.2 g of the desired compound.

EXAMPLE 14

5-Hydroxy-N,N,N-trimethyl-8-(phenylmethoxy)-4,6,10-trioxa-5-phosphahexacosan-2-aminium,5-oxide, hydroxide, inner salt As 25 ml portion of acetonitrile was added to a steel bomb cooled in an ice bath. A 7.2 g portion of 3-(hexadecyloxy)-2-(phenylmethoxy)phosphoric acid, 2-bromopropyl ester was dissolved in 25 ml of ice-cold trimethylamine by swirling in an ice bath and added to the acetonitrile in the bomb. A 25 ml portion of trimethylamine and 10 ml of chloroform were added, the bomb was sealed and heated at 60°–65° C. overnight. The mixture was cooled, removed from the bomb, taken to dryness and dissolved in 25 ml of trimethylamine. A 25 ml portion dimethylformamide and 25 ml of trimethylamine were added, the mixture placed in the bomb and heated at 70° C. overnight. The contents were cooled, removed from the bomb, taken to near dryness, dissolved in 25 ml of chloroform and 25 ml of methanol and 2.5 ml of 30% hydrogen peroxide added. A 1.62 g portion of silver carbonate was added, the mixture stirred for 2 hours, filtered through diatomaceous earth, washed with methanol and taken to dryness giving a syrup. This syrup was dissolved in 10% methanol in chlorofom and chromatographed on silica gel removing the more mobile impurities by eluting with 10%, 20% and finally 30% methanol in chloroform. The column was then eluted with chloroform:methanol:water (65:35:6). This eluate was taken to dryness evaporated twice with toluene giving a glass which was triturated with ether, giving 1.27 g of the desired compound as a white solid.

EXAMPLE 15

5,8-Dihydroxy-N,N,N-trimethyl-4,6,10-trioxa-5-phosphahexacosan-2-aminium,5-oxide, hydroxide, inner salt A solution of 1.7 g of 5-hydroxy-N,N,N-trimethyl-8-(phenylmethoxy)-4,6,10-trioxa-5-phosphahexacosan-2-aminium, 5-oxide, hydroxide, inner salt in 40 ml of methanol and 40 ml of glacial acetic acid was hyrogenated with 0.7 g of 5% palladium on carbon in a Parr apparatus overnight at a initial pressure of 25 psi. This mixture was filtered through diatomaceous earth, washed with methanol, the mother liquor taken to dryness and evaporated twice from toluene. The resulting glass was triturated with ether and the solid collected, giving 1.52 g of the desired compound as a white solid, mp 95° C.

EXAMPLE 16

8-(Acetyloxy)-5-hydroxy-N,N,N-trimethyl-4,6,10-trioxa-5-phosphahexacosan-2-aminium, 5-oxide, hydroxide, inner salt A solution of 1.4 g of 5,8-diydroxy-N,N,N-trimethyl-4,6,10-trioxa-5-phosphahexacosan-2-aminium, 5-oxide, hydroxide, inner salt in 70 ml of dry chloroform containing 6.7 ml of acetic anhydride and 3.9 ml of triethylamine was stirred at reflux temperature under argon for 5 hours, then taken to dryness. The residue was evaporated three times from toluene giving a glass. This glass was triturated with 50 ml of ether, refrigerated overnight and the solvents removed. The residue was dissolved in 10 ml of 20% methanol in chloroform and applied to a column filled with silica gel which had been slurried in 20% methanol in chloroform. The column was eluted with 500 ml of 20% methanol in chloroform, then 500 ml of 30% methanol in chloroform to remove mobile impurities and then with chloroform:methanol:water (65:35:6) to remove the product. Fraction 8–18 were combined and evaporated. The residue was evaporated twice from toluene then triturated with ether, giving 1.20 g of the desired product as a white solid, mp 200°–205° C. (dec.).

EXAMPLE 17

1-(Hexadecyloxy)-3-[(4-methoxyphenyl)diphenylmethoxy]-2-propanol

To a mixture of 84.5 g of 3-(hexadecyloxy)-1,2-propanediol in 265 ml of dry pyridine, stirred in an ice bath under nitrogen, was added in a steady stream a solution of 115.5 g of 4-methoxytrityl chloride in 150 ml of dry tetrahydrofuran. This mixture was stirred in the ice bath for 30 minutes, then at room temperature for 2 hours, then refrigerated at 0° C. overnight. The mixture was concentrated to remove the volatile solvents. The residual solution was dissolved in 400 ml of chloroform, washed twice with 200 ml portions of 10% aqueous sodium bicarbonate and twice with 200 ml portions of water, dried and evaporated. The residue was evaporated twice from toluene, taken up in ether, chilled and filtered. The filtrate was taken to dryness, giving a syrup. A 30 g portion of this syrup was dissolved in petroleum ether and chromatographed on a silica gel column eluting with 20% ether in petroleum ether. The product fractions 6–20 (200 ml each) were combined and evaporated, giving 21 g of the desired compound.

EXAMPLE 18

1-(Hexadecyloxy)-3-[(4-methoxyphenyl)diphenylmethoxy]-2-propanol, acetate

A solution of 20 g of 1-(hexadecyloxy)-3-[(4-methoxyphenyl)diphenylmethoxy]-2-propanol in 70 ml of dry pyridine and 20 ml of acetic anhydride was allowed to stand in a stoppered flask for 24 hours. A 300 ml portion of ice and water was added and the mixture was extracted with two 150 ml portions of chloroform. The chloroform extracts were combined, washed with two 150 ml portions of 10% aqueous sodium bicarbonate, then saturated saline, dried and taken to dryness. The residue was evaporated from toluene, giving a syrup. This syrup was chromatographed on silica gel equilibrated with 120 ml of 15% ether in petroleum ether. The column was eluted with 15% ether in petroleum ether collecting 400 ml. The top 6 inches and bottom 16 inches were cut from the column. The remainder of the column was cut into thirty-five 1 inch segments.

Cuts 3–20 were combined in ether, then the ether was removed, giving 18.4 g of the desired compound as a pale yellow syrup.

EXAMPLE 19

3-(Hexadecyloxy)-1,2-propanediol, 2-acetate

A 200 g portion of silicic acid was suspended five times in distilled water, with the water decanted each time to remove fine particles. Residual water was filtered off on a sintered glass funnel. The silicic acid was then mixed thoroughly with a hot saturated solution of 20 g of boric acid in 100 ml of water, then air dried and activated at 120° C. for 24 hours.

A 100 g portion of the activated silicic acid-boric acid mixture was suspended in 400 ml of petroleum ether and poured onto a 60×3 cm glass column containing 50 ml of petroleum ether. A 10 g portion of 1-(hexadecyloxy)-3-[(4-methoxyphenyl)diphenylmethoxy]-2-propanol, acetate was dissolved in 25 ml of petroleum ether and added to the column. The column was eluted first with 2550 ml of petroleum ether, then with 2825 ml of 5% ether in petroleum ether to remove more mobile impurities and finally with 3000 ml of 50% ether in petroleum ether, giving 4.54 g of the desired compound as a waxy solid.

EXAMPLE 20

2-(Acetyloxy)3-(hexadecyloxy)propyl-2-bromo-2-phenylethylphosphoric acid, ester

To a solution of 3.11 g of 3-(hexadecyloxy)-1,2-propanediol, 2-acetate in 40 ml of carbon tetrachloride, cooled in an ice bath under argon was added 3.9 g of phosphorodichloridic acid, 2-bromo-2-phenylethyl ester in 5 ml of carbon tetrachloride followed by 1.3 g of triethylamine in 5 ml of carbon tetrachloride. This mixture was stirred in the ice bath for 30 minutes, then at room temperature overnight, then filtered and washed with carbon tetrachloride. The mother liquor was taken to dryness. The residue was stirred in 100 ml of tetrahydrofuran and 100 ml of 0.5M aqueous sodium acetate for 2 hours, then the tetrahydrofuran was removed in vacuo. The aqueous remainder was acidified with hydrochloric acid and extracted three times with ether. The ether extracts were combined, washed with saturated aqueous sodium chloride, dried and taken to dryness leaving a syrup. This syrup was chromatographed on magnesium silicate, eluting the mobile impurities with chloroform and then eluting the desired compound with 10% methanol in chloroform, giving 911 mg.

EXAMPLE 21

7-(Acetyloxy)-4-hydroxy-N,N,N-trimethyl-1-phenyl-3,5,9-trioxa-4-phosphapentacosan-1-aminium, 4-oxide, hydroxide inner salt To a solution of 911 mg of 2-(acetyloxy)-3-(hexadecyloxy)propyl-phosphoric acid, 2-bromo-2-phenylethyl ester in 3 ml of dimethylformamide and 2 ml of chloroform was added 20 ml of trimethylamine. This mixture was heated in a bomb at 100° C. overnight, then cooled, the contents removed and the volatile solvents evaporated. A 20 ml portion of methanol and 220 mg of silver carbonate were added, the mixture stirred for 1.5 hours, filtered through diatomaceous earth and washed with methanol. The solvents were removed and the syrup dissolved in chloroform and chromatographed on silica gel which had been slurried in 20% methanol in chloroform. The column was eluted with 300 ml of 20% methanol in chloroform, then 750 ml of 30% methanol in chloroform to remove mobile impurities, then the product was eluted with chloroform:methanol:water (65:35:6). The product fractions 5,6 and 7 were combined, taken to dryness, evaporated twice from toluene, added to ether and refrigerated under argon giving 492 mg of the desired product.

EXAMPLE 22

Phosphoric acid, 2-(acetyloxy)-3-(hexadecyloxy)propyl-3-(bromoethyl)-phenyl ester To a solution of 2.86 g of 3-(hexadecyloxy)-1,2-propanediol, 2-acetate in 30 ml of carbon tetrachloride was added 2.43 g of phosphorodichloridic acid, 3-(bromomethyl)-phenyl ester in 5 ml of carbon tetrachloride under argon. This solution was stirred in an ice bath and a solution of 809 mg of triethylamine in 5 ml of carbon tetrachloride was added dropwise. The mixture was then stirred at room temperature for 2 hours, toluene was added and the mixture filtered and washed with toluene. The mother liquor was taken to dryness. To the residual oil was added 40 ml of tetrahydrofuran and 40 ml of 0.5M aqueous sodium acetate. This mixture was stirred for 24 hours, placed in a freezer, concentrated in vacuo to remove the tetrahydrofuran and acidified with cold 0.5N hydrochloric acid. This mixture was extracted twice with ether. The extracts were combined, washed with saturated sodium chloride solution, dried and evaporated giving a syrup. This syrup was chromatographed on magnesium silicate, eluting first with chloroform to remove mobile impurities, then with 10% methanol in chloroform. Cuts 6,7 and 8 were combined and evaporated, giving 2.2 g of the desired compound.

EXAMPLE 23

3-[[[2-(Acetyloxy)-3-(hexadecyloxy)propoxy]hydroxyphosphinyl]oxy]-N,N,N-trimethylbenzenemethanaminium, hydroxide inner salt A 2.2 g portion of phosphoric acid, 2-(acetyloxy)-3-(hexadecyloxy)propyl-3-(bromomethyl)phenyl ester was dissolved in 4 ml of dry dimethylformamide. A 15 ml portion of 33% trimethylamine in acetonitrile was added, the mixture was stirred for 20 minutes, then 10 ml of 33% trimethylamine in acetonitrile was added and the mixture was stirred in a 45° C. water bath for 20 minutes. The mixture was then stoppered and refrigerated. The solvents were removed and the residue triturated with ether giving a white solid. The solid was dissolved in 10 ml of chloroform:methanol:water (65:35:3) and chromatographed on silica gel which was wet with the same solvent system. The column was developed with the same solvent system. The eluate was evaporated to dryness, then evaporated twice from toluene, taken up in 20 ml of methanol and filtered through diatomaceous earth. The filtrate was evaporated and the residue triturated with ether and refrigerated for 48 hours. The solid was collected, giving 1.196 g of the desired product as a white solid.

EXAMPLE 24

1-[(4-Methoxyphenyl)diphenylmethoxy]-3-(3-tetradecylphenoxy)-2-propanol

A solution of 25.94 g of 4-methoxytrityl chloride in 15 ml of dry tetrahydrofuran was added to a stirred solution of 21.84 g of 3-(3-tetradecylphenoxy)-1,2-propanediol in 40 ml of pyridine under argon. This mixture was stirred overnight, the solvents removed under reduced pressure and the residue dissolved in chloroform. This solution was washed with saturated aqueous sodium bicarbonate, then water, dried and evaporated, giving 34.3 g of the desired compound.

EXAMPLE 25

1-[(4-Methoxyphenyl)diphenylmethoxy]-3-(3-tetradecylphenoxy)-2-propanol, acetate A mixture of 63.6 g of 1-[(4-methoxyphenyl)diphenylmethoxy]-3-(3-tetradecylphenoxy)-2-propanol, 60 ml of acetic anhydride and 200 ml of pyridine was stirred for 72 hours, then poured onto ice and extracted several times with chloroform. The chloroform extracts were combined, washed three times with saturated aqueous sodium bicarbonate, then with water, dried and the solvent removed under reduced pressure. The residue was evaporated three times from 200 ml portions of toluene, giving 62.6 g of the desired compound.

EXAMPLE 26

3-(3-Tetradecylphenoxy)-1,2-propanediol, 2-acetate

A silicic acid-boric acid column was prepared as described in Example 19 using 320 g of the powder.

A 30 g portion of 1-[(4-methoxyphenyl)diphenylmethoxy]-3-(3-tetradecylphenoxy)-2-propanol, acetate was dissolved in 30 ml of petroleum ether and introduced to the column. The column was eluted with 3 liters of petroleum ether, then 4.5 liters of petroleum ether:ether(95:5) to remove impurities and then with petroleum ether:ether (3:1) to elute the desired compound, giving 14.3 g.

EXAMPLE 27

2-(Acetyloxy)-3-(3-tetradecylphenoxy)propyl phosphoric acid, 2-bromopropyl ester A mixture of 812 mg of 3-(3-tetradecylphenoxy)-1,2-propanediol, 2-acetate, 610 mg of phosphorodichloridic acid 2-bromopropyl ester and 243 mg of triethylamine in 30 ml of carbon tetrachloride was stirred under argon for 2 hours, then filtered through diatomaceous earth and the solvent removed under reduced pressure. The residue was dissolved in 15 ml of tetrahydrofuran and 15 ml of 0.5M aqueous sodium acetate was added. The mixture was stirred for 1 hour, then extracted several times with ethyl acetate. The organic extracts were combined, dried and evaporated. The residue was purified by column chromatography on magnesium silicate eluting impurities with chloroform, then chloroform:methanol (9:1), then the desired compound with chloroform:methanol (7:3), giving 900 mg.

EXAMPLE 28

7-Hydroxy-N,N,N-trimethyl-2-oxo-4-[(3-tetradecylphenoxy)methyl]-3,6,8-trioxa-7-phosphaundecan-10-aminium, 7-oxide, hydroxide, inner salt A mixture of 606 mg of 2-(acetyloxy)-3-(3-tetradecylphenoxy)propyl phosporic acid, 2-bromopropyl ester, 10 ml of trimethylamine, 5 ml of acetonitrile and 5 ml of chloroform was heated in a steel bomb at 75°–90° C. for 24 hours, then cooled and the solvents removed. The residue was purified on a silica gel column, eluting impurities with chloroform:methanol (9:1), then (1:1) and then eluting the desired product with chloroform:methanol:water (6:4:05).

EXAMPLE 29

4-Tetradecylphenol, acetate

A mixture of 290 mg of 4-tetradecylphenol, 2 ml of acetic acid and 5 ml of pyridine was stirred for 24 hours, then diluted with ether and washed with aqueous sodium bicarbonate. The mixture was dried and the solvents removed, giving 256 mg of the desired compound, mp 32°–34° C.

EXAMPLE 30

1-(2-Hydroxy-5-tetradecylphenyl)ethanone

A 900 mg portion of 4-tetradecylphenol, acetate was heated at 70° C. under argon and 720 mg of aluminum trichloride was added portionwise. After 2 hours the temperature was raised to 120° C. and the mixture was heated at this temperature for 45 minutes. The mixture was then cooled, diluted with chloroform, washed with 50% aqueous hydrochloric acid then water and dried. The solvents were removed and the residue recrystallized from ether-methanol, giving 850 mg of the desired compound, mp 38.5°–39.5° C.

EXAMPLE 31

2-Ethyl-4-tetradecylphenol

A mixture of 23 g of 1-(2-hydroxy-5-tetradecylphenyl)ethanone, 5 g of 5% palladium on carbon catalyst, 10 ml of concentrated hydrochloric acid, 100 ml of water and 100 ml of glacial acetic acid was warmed to 50° C. and then hydrogenated in a Parr apparatus for 24 hours. This mixture was filtered, the solvent removed ad the residue dissolved in ether. The ether solution was washed with water, then a small amount of dilute aqueous sodium bicarbonate and dried. The residue was purified by HPLC, giving 16 g of the desired compound, mp 45.5°–46.5° C.

EXAMPLE 32

4-[(2-Ethyl-4-tetradecylphenoxy)methyl]-2,2-dimethyl-1,3-dioxolane

To a suspension of 2.53 g of prewashed 50% sodium hydride in 130 ml of dimethylformamide was added dropwise a solution of 11.99 g of 2-ethyl-4-tetradecylphenol in dimethylformamide. The resulting suspension was heated at 80° C. for ½ hour, then allowed to cool and 10.29 g the mesylate of solketal was added. The mixture was heated at reflux for 3 hours, then cooled quenched slowly with water and extracted several times with ether. The ether extracts were combined, washed with brine, dried and the solvents evaporated, giving 16.1 g of the desired compound, mp 34°–38° C.

EXAMPLE 33

3-(2-Ethyl-4-tetradecylphenoxy)-1,2-propanediol

A mixture of 15.55 g of 4-[(2-ethyl-4-tetradecylphenoxy)methyl]-2,2-dimethyl-1,3-dioxolane, 10 ml of 5% hydrochloric acid and 300 ml of tetrahydrofuran was heated at reflux for 4 hours, then cooled and ½ of the solvent evaporated at reduced pressure. The remainder was diluted with ethyl acetate, washed with aqueous sodium bicarbonate, dried and the solvents evaporated. The residue was chromatographed on silica gel, eluting first with hexane:ethyl acetate (8:1), then (4:1), giving 12.1 g of the desired compound, mp 55°–56° C.

EXAMPLE 34

1-(2-Ethyl-4-tetradecylphenoxy)-3-(triphenylmethoxy)-2-propanol

A mixture of 11.68 g of 3-(2-ethyl-4-tetradecylphenoxy)-1,2-propanediol, 14.95 g of trityl chloride and 40 ml pryridine was stirred for 72 hours, then diluted with chloroform, washed with two 100 ml portions of aqueous sodium bicarbonate, then water and dried. The solvents were evaporated under reduced pressure and the residue evaporated with toluene. This residue was then diluted with hexanes and the solid which formed collected giving 18 g of the desired compound.

EXAMPLE 35

2-Ethyl-1[2-(phenylmethoxy)-3-(triphenylmethoxy)-propoxy]-4-tetradecylbenzene

To a suspension of 2.016 g of prewashed sodium hydride in 125 ml of dimethylformamide was added dropwise a solution of 17.75 g of 1-(2-ethyl-4-tetradecylphenoxy)-3-(triphenylmethoxy)-2-propanol in 125 ml of dimethylformamide. This mixture was stirred 15 minutes, then 7.198 g of benzyl bromide was added and stirring was continued for an additional 3 hours. The reaction mixture was quenched slowly with water and then extracted several times with ether. The ether extracts were combined, washed with water, dried and the solvent evaporated, giving 19.9 g of the desired compound.

EXAMPLE 36

2-(Phenylmethoxy)-3-(2-ethyl-4-tetradecylphenoxy)-1-propanol

A stream of dry hydrogen chloride gas was bubbled into 200 ml of chloroform at 0° C. for 20 minutes, then a solution of 19.548 g of 2-ethyl-1-[2-(phenylmethoxy)-3-(triphenylmethoxy)propoxy]-4-tetradecylbenzene in 100 ml of chloroform was added slowly. This solution was stirred at 0° C. for 2.5 hours, then solid sodium bicarbonate was added and stirring continued for 1 hour. The mixture was filtered and the chloroform removed under reduced pressure. The residue was diluted with ether, washed with saturated aqueous sodium bicarbonate, dried and the solvent removed. The residue was chromatographed on silica gel, eluting with hexane:ether (18:1), giving 12.5 g of the desired compound, mp 46°–47° C.

EXAMPLE 37

Hexanoic acid, 4-tetradecylphenyl ester

A mixture of 43.5 g of 4-tetradecylphenol, 34.8 g of hexanoic anhydride and 120 ml of pyridine was stirred for 3 days, then quenched with water and extracted with chloroform. The chloroform extract was washed several times with aqueous sodium bicarbonate, dried and the solvents removed. The residue was recrystallized from ether-methanol, giving 53.2 g of the desired compound.

EXAMPLE 38

1-(2-Hydroxy-5-tetradecylphenyl)-1-hexanone

To a melted liquid of 38.8 g of hexanoic acid, 4-tetradecylphenyl ester at 80°–95° C. was added 26.67 g of aluminum chloride in small portions over a period of 2 hours. This mixture was heated for an additional hour, then allowed to cool, diluted with ether and poured onto ice containing 10 ml of concentrated hydrochloric acid. The organic layer was washed with water, dried and the solvent evaporated. The residue was chromatographed on silica gel, eluting with hexane:ethyl acetate (50:1), giving 33 g of the desired compound, mp 41°–42° C.

EXAMPLE 39

2-Hexyl-4-tetradecylphenol

A mixture of 31.04 g of 1-(2-hydroxy-5-tetradecylphenyl)-1-hexanone, 8.4 g of 5% palladium on carbon, 5 ml of concentrated hydrochloric acid, 95 ml of water and 100 ml of glacial acetic acid was hydrogenated in a Parr apparatus for 16 hours, then filtered and the solvents removed. The residue was chromatographed on silica gel, eluting with hexane:ethyl acetate (40:1), giving 12.3 g of the desired compound.

EXAMPLE 40

4-[(2-Hexyl-4-tetradecylphenoxy)methyl]-2,2 dimethyl-1,3-dioxolane

To a suspension of 2.27 g of prewashed 50% sodium hydride in 65 ml of dimethylformamide was added dropwise a solution of 11.78 g of 2-hexyl-4-tetradecylphenol in 65 ml of dimethylformamide. This mixture was heated for ½ hour, then 8.61 g of the mesylate of solketal was added. The mixture was heated at reflux for 3 hours, cooled, quenched carefully with water and extracted several times with ether. The ether extracts were combined, dried and the solvent evaporated, giving 15 g of the desired compound.

EXAMPLE 41

3-(2-Hexyl-4-tetradecylphenoxy)-1,2-propanediol

A mixture of 13.6 g of 4-[(2-hexyl-4-tetradecylphenoxy)methyl]-2,2-dimethyl-1,3-dioxolane, 10 ml of 5% hydrochloric acid and 250 ml of tetrahydrofuran was heated at reflux for 4 hours, then allowed to cool and the tetrahydrofuran removed under reduced pressure. The mixture was then extracted several times with ethyl acetate. The organic extracts were combined, washed with aqueous sodium bicarbonate, dried and the solvent evaporated, giving 12.3 g of the desired compound.

EXAMPLE 42

1-(2-Hexyl-4-tetradecylphenoxy)-3-(triphenylmethoxy)-2-propanol

A mixture of 11.64 g of 3-(2-hexyl-4-tetradecylphenoxy)-1,2-propanediol, 12.32 g of trityl chloride and 40 ml of pyridine was stirred for 24 hours, then diluted with chloroform, washed with aqueous sodium bicarbonate, water, dried and the solvents evaporated under reduced pressure. The residue was coevaporated with toluene, giving 14.6 g of the desired compound.

EXAMPLE 43

2-Hexyl-1-[2-phenylmethoxy)-3-(triphenylmethoxy)propoxy]-4-tetradecylbenzene A solution of 12.21 g of 1-(2-hexyl-4-tetradecylphenoxy)-3-(triphenylmethoxy)-2-propanol in 50 ml of dimethylformamide was added to a suspension of 1.27 g of prewashed 50% sodium hydride in 50 ml of dimethylformamide. This mixture was stirred for 15 minutes, then 3.94 g of benzyl bromide was added and stirring continued for 3 hours. This mixture was diluted with ether, washed with water and brine, dried and the solvent evaporated, giving 13.08 g of the desired compound.

EXAMPLE 44

3-(2-Hexyl-4-tetradecylphenoxy)-2-(phenylmethoxy)-1-propanol

A solution of 11.9 g of 2-hexyl-1-[2-(phenylmethoxy)-3-(triphenylmethoxy)propoxy]-4-tetradecylbenzene in 250 ml of chloroform was cooled to 0° C. A stream of dry hydrogen chloride gas was bubbled into the solution for ½ hour, then the mixture was stirred for 2 hours at 0° C. Solid sodium bicarbonate was added, the mixture stirred for 3 hours, then filtered and the chloroform evaporated. The residue was dissolved in ether, washed with aqueous sodium bicarbonate, dried and the residue chromatographed on silica gel. The column was eluted with hexane:ethyl acetate, giving 5.8 g of the desired compound, mp 32°–33° C.

EXAMPLE 45

Hexanoic acid, 3-tetradecylphenyl ester

To a solution of 10.73 g of 3-tetradecylphenol in 30 ml of pyridine was added 8.02 g of hexanoic anhydride. The mixture was stirred 24 hours, then diluted with chloroform, washed with water, then saturated aqueous sodium bicarbonate, dried and the solvent evaporated, giving 14.01 g of the desired compound.

EXAMPLE 46

1-(2-Hydroxy-4-tetradecylphenyl)-1-hexanone

A 14.28 g portion of hexanoic acid, 3-tetradecylphenyl ester was heated to 90°–100° C., then 9.81 g of aluminum chloride was added in portions over 2 hours. Heating was continued for an additional hour, then the mixture was allowed to cool, diluted with ether and poured onto a mixture of ice and concentrated hydrochloric acid. The ether layer was washed with water, then dried and the solvent removed, giving 7 g of the desired compound, mp 44°–45° C.

EXAMPLE 47

2-Hexyl-5-tetradecylphenol

A mixture of 16.99 g of 1-(2-hydroxy-4-tetradecylphenyl)-1-hexanone, 4 g of 5% palladium on carbon catalyst, 100 ml of glacial acetic acid and 50 ml of methanol was hydrogenated in a Parr apparatus for 24 hours. The mixture was filtered, the solvents removed and the residue dissolved in ether, washed with water and dried. This crude material was chromatographed on silica gel, eluting with hexane:ethyl acetate (10:1), giving 15.3 g of the desired product, mp 43°–45° C.

EXAMPLE 48

3-[(2-Hexyl-5-tetradecylphenoxy)methyl]-2,2-dimethyl-1,3-dioxolane

To a suspension of 2.77 g of prewashed sodium hydride in 75 ml of dimethylformamide was added dropwise a solution of 14.4 g of 2-hexyl-5-tetradecylphenol in 75 ml of dimethylformamide. This mixture was refluxed for ½ hour, then 10.5 g of the mesylate of solketal was added and the mixture was refluxed for an additional 3 hours. After cooling the mixture was quenched slowly with water and then extracted several times with ether. The ether extracts were combined, washed with water, brine, dried and evaporated, giving 18 g of the desired compound.

EXAMPLE 49

3-(2-Hexyl-5-tetradecylphenoxy)1,2-propanediol

A mixture of 17.47 g of 3-[(2-hexyl-5-tetradecylphenoxy)methyl]-2,2-dimethyl-1,3-dioxolane, 10 ml of 5% hydrochloric acid and 150 ml of tetrahydrofuran was refluxed for 5 hours, then cooled and the tetrahydrofuran removed under reduced pressure. The remainder was extracted several times with ethyl acetate. The organic extracts were combined, washed with aqueous sodium bicarbonate, dried and the solvent evaporated. The residue was chromatographed on silica gel, eluting with hexane:ethyl acetate, giving 13.6 g of the desired compound, mp 46°–47° C.

EXAMPLE 50

1-(2-Hexyl-5-tetradecylphenoxy)-3-(triphenylmethoxy)-2-propanol

A mixture of 12.77 g of 3-(2-hexyl-5-tetradecylphenoxy)-1,2-propanediol, 13.5 g of trityl chloride and 40 ml of pyridine was stirred for 24 hours, then diluted with chloroform, washed with aqueous sodium bicarbonate, water and dried. This crude material was chromatographed on silica gel, eluting with 17% ethyl acetate in hexane, giving 14 g of the desired compound.

EXAMPLE 51

1-Hexyl-2-[2-(phenylmethoxy)-3-(triphenylmethoxy)propoxy]-4-tetradecylbenzene A 13.8 g portion of 1-(2-hexyl-5-tetradecylphenoxy)-3-(triphenylmethoxy)-2-propanol in 40 ml of dimethylformamide was added dropwise to a suspension of 14.5 g of prewashed 50% sodium hydride in 40 ml of dimethylformamide and the mixture was stirred 15 minutes. A 4.45 g portion of benzyl bromide was added and the mixture was stirred an additional 3 hours. This mixture was quenched slowly with water and then extracted several times with ether. The ether extracts were combined, washed with water, brine, dried and evaporated, giving 15 g of the desired compound.

EXAMPLE 52

3-(2-Hexyl-5-tetradecylphenoxy)-2-(phenylmethoxy)-1-propanol

A 500 ml portion of chloroform was cooled to 0° C. and dry hydrogen chloride gas was bubbled in for 10 minutes, then an ice-cold solution of 14.43 g of 1-hexyl-2-[2-(phenylmethoxy)-3-(triphenylmethoxy)propoxy]-4-tetradecylbenzene in chloroform was added. The mixture was stirred at 0° C. for 1.5 hours, then solid sodium bicarbonate was added and stirring continued for 1 hour at room temperature. The mixture was filtered, the solvent removed under reduced pressure and the residue purified by chromatography, eluting impurities with 1% ethyl acetate in hexane, then eluting the desired compound in ethyl acetate:hexane (1:8), giving 8.8 g of the desired product.

EXAMPLE 53

3-Tetradecylphenol, acetate

A mixture of 18.85 g of 3-tetradecylphenol, 20 ml of acetic anhydride and 60 ml of pyridine was stirred for 16 hours, then diluted with chloroform, washed with aqueous sodium bicarbonate, dried and the solvent removed by evaporation with toluene, giving 21 g of the desired compound.

EXAMPLE 54

1-(2-Hydroxy-4-tetradecylphenyl)ethanone

A 20 g portion of 3-tetradecylphenol, acetate was heated at 110° C. and 8.4 g of aluminum chloride was added in portions over a 3 hour period. The mixture was allowed to cool, then diluted with ether, poured onto ice containing 10 ml of concentrated hydrochloric acid and extracted several times with ether. The ether extracts were combined, washed with water, brine and dried. The crude material was chromatographed on silica gel, eluting with hexane:ethyl acetate (50:1), giving 15.8 g of the desired compound, mp 45°–46° C.

EXAMPLE 55

2-Ethyl-5-tetradecylphenol

A 15.6 g portion of 1-(2-hydroxy-4-tetradecylphenyl)-ethanone was heated in a mixture of 120 ml of acetic acid and 30 ml of methanol until solution was complete. A 4 g portion of 5% palladium on carbon was added and the mixture was hydrogenated in a Parr apparatus for 18 hours. The mixture was then filtered through diatomaceous earth and the solvents removed under reduced pressure, giving 14.5 g of the desired compound, mp 59°–60° C.

EXAMPLE 56

4-[(2-Ethyl-5-tetradecylphenoxy)methyl]-2,2-dimethyl-1,3-dioxolane

A solution of 11.29 g of 2-ethyl-5-tetradecylphenol in 50 ml of dimethylformamide was added dropwise to a suspension of 2.56 g of prewashed 50% sodium hydride in 50 ml of dimethylformamide. After bubbling ceased the mixture was heated for ½ hour, then 11.13 g of the mesylate of solketal was added. This mixture was refluxed for 3 hours, then allowed to cool, diluted with ether, washed with water, dried and the solvents evaporated, giving 15 g of the desired compound.

EXAMPLE 57

3-(2-Ethyl-5-tetradecylphenoxy)-1,2-propanediol

A mixture of 14.2 g of 4-[(2-ethyl-5-tetradecylphenoxy)methyl]-2,2-dimethyl-1,3-dioxolane, 50 ml of 5% hydrochloric acid and 100 ml of tetrahydrofuran was heated at reflux for 8 hours, then allowed to cool and the tetrahydrofuran removed under reduced pressure. Ethyl acetate was added, the mixture washed with water, dried and the solvents removed. The residue was chromatographed on silica gel, eluting impurities with hexane:ethyl acetate (16:1) and then (4:1) to elute the desired compound, giving 11 g, 55.5°–56.5° C.

EXAMPLE 58

1-(2-Ethyl-5-tetradecylphenoxy)-3-[(4-methoxyphenyl)diphenylmethoxy]-2-propanol A mixture of 10.58 g of 3-(2-ethyl-5-tetradecylphenoxy)-1,2-propanediol, 9.59 g of p-methoxytrityl chloride, 20 ml of pyridine and 10 ml of tetrahydrofuran was stirred for 3 days. The tetrahydrofuran was removed under reduced pressure. The residue was diluted with chloroform, washed several times with saturated aqueous sodium bicarbonate, dried, filtered and the the solvents evaporated. The residue was coevaporated with toluene, giving 17.65 g of the desired compound.

EXAMPLE 59

1-Ethyl-2-[3-[(4-methoxyphenyl)diphenylmethoxy]-2-(phenylmethoxy)propoxy]-4-tetradecylbenzene To a suspension of 1.87 g of prewashed 50% sodium hydride in 50 ml of dimethylformamide was added a solution of 17.26 g of 1-(2-ethyl-5-tetradecylphenoxy)-3-[(4-methoxyphenyl)diphenylmethoxy]-2-propanol in 50 ml of dimethylformamide. This mixture was stirred for 15 minutes, then 5.79 g of benzyl bromide was added. This mixture was stirred 3 hours, quenched slowly with water and extracted several times with ether. The ether extracts were combined, washed with water, dried and the solvent removed, giving 19.1 g of the desired compound.

EXAMPLE 60

3-(2-Ethyl-5-tetradecylphenoxy)2-(phenylmethoxy)-1-propanol

A stream of dry hydrogen chloride gas was bubbled into 500 ml of chloroform at 0° C. for 1 hour, then a cooled solution of 18.85 g of 1-ethyl-2-[3-[(4-methoxyphenyl)diphenylmethoxy]-2-(phenylmethoxy)propoxy]-4-tetradecylbenzene in chloroform was added. The mixture was stirred 3 hours, then dry sodium bicarbonate was added. This mixture was stirred for 1 hour, filtered and the solvent removed. The residue was purified on silica gel, eluting with hexane:ethyl acetate (8:1), giving 10 01 g of the desired compound.

Included in this invention are compounds of the formula:

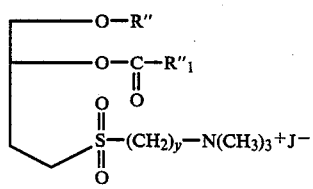

44 wherein $R''$ is a $C_2$–$C_{20}$ alkyl group, $R_1''$ is a $C_1$ to $C_4$ alkyl group, $y$ is an integer from 2 to 10 and $J^-$ is a pharmacologically acceptable anion. The compounds represented by the above formula are prepared as described hereinbelow in Flowsheet H.

According to the reactions outlined hereinbelow in Flowsheet H alkylation of an alcohol 37 with chloroacetic acid is accomplished by the prior formation of the sodium salt of the acid by addition to a suspension of excess sodium hydride in toluene; addition of the alcohol and refluxing furnishes, after work up, the carboxylic acid 38. The reaction of 38 with an excess of vinyl lithium in dimethoxyethane gives the unsaturated ketone 39. Compound 40 is prepared in a one pot reaction involving a sequential Michael addition and reduction. Thus, addition of an excess of a N,N-dimethylamino thiol 41 to an ethanol solution of 39 followed by the portionwise addition of sodium borohydride gives 40. Acylation of 40 with an anhydride and triethylamine gives the acyl derivative 42. The amino group of 42 is quarternized to give 43 by the reaction of an etheral solution of 42 with one equivalent of methyl iodide at room temperature for one to five days. Finally, oxidation of 43 to the sulfone is accomplished with 40% peracetic acid in methylene chloride at room temperature to give, after treatment with the desired anion exchange resin, the compounds of the invention of formula 44.

FLOWSHEET H

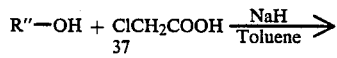

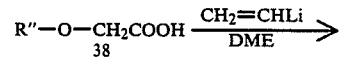

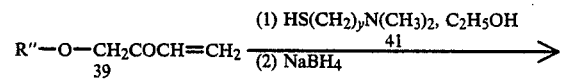

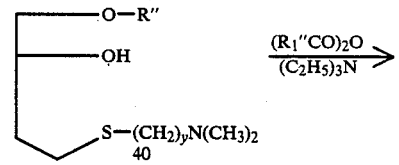

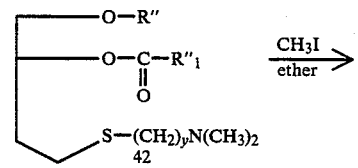

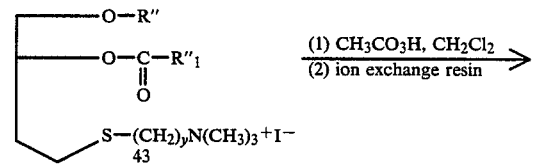

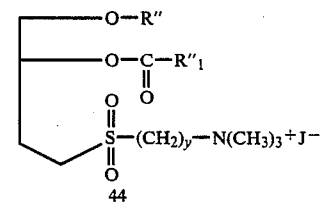

44

EXAMPLE 61

1-(Hexadecyloxy)acetic acid

To a suspension of 44.5 g of washed (hexane) 50% sodium hydride mineral oil dispersion in 500 ml of toluene was added with mechanical stirring under argon a solution of 46.8 g of chloroacetic acid in 200 ml of toluene over 1 hour. A solution of 100 g of 1-hexadecanol in 200 ml of toluene was then added over 15 minutes. The mixture was stirred at reflux 40 hours, cooled to room temperature, and acidified with dilute hydrochloric acid. The mixture was heated until all solid dissolved. The hot organic layer was dried over magnesium sulfate and cooled giving 84.5 g of product as a colorless solid: mp 64°–66° C.

EXAMPLE 62

1-(Hexadecyloxy)-3-buten-2-one

To a solution of 88 g of 1-(hexadecyloxy)acetic acid in 800 ml of DME was added dropwise under argon with stirring at 0° C., 280 ml of 2.3M vinyl lithium in THF. The mixture was stirred at 40° C. overnight. TLC of an aliquot quenched with dilute hydrochloric acid indicated that some starting material remained unreacted. The solution was cooled to room temperature and another 180 ml of vinyl lithium solution was added. The mixture was maintained at 40° C. for 18 hours. The mixture was cooled to room temperature and pumped into dilute hydrochloric acid with ice cooling under argon. The mixture was saturated with sodium chloride and the organic layer was separated. The aqueous layer was extracted with ether. The combined organic solutions were dried over magnesium sulfate and the solvent was removed. The product was chromatographed via preparative HPLC (hexane-ether) giving 26.7 g of a white solid. TLC showed a major component which gave a yellow spot on treatment with 2,4-dinitrophenylhydrazine spray, and a minor component with slightly lower retention time which did not react with the reagent spray. Obtained in this manner the product was used in the next step without additional purification.

EXAMPLE 63

4-[[3-(Dimethylamino)propyl]thio]-1-(hexadecyloxy)-2-butanol

A solution of 26.5 g of 1-(hexadecyloxy)-3-buten-2-one in 200 ml of ethanol was warmed on a steam bath until all solid dissolved. To the solution was added 26.9 g of 3-N,N-dimethylaminopropanthiol. After stirring 1 hour, 3.23 g of solid sodium borohydride was added portionwise over 30 minutes. After stirring an additional 1½ hours, the solution was poured into water and extracted with ether. The ether solution was dried over magnesium sulfate. Solvent and excess reagent were removed at reduced pressure. The residue was chromatographed on silica gel via preparative HPLC eluting with chloroform-methanol (9:1) giving 13.7 g of product as a colorless solid: mp 30°-32° C.

EXAMPLE 64

4-[[(3-(Dimethylamino)propyl]thio]-1-(hexadecyloxy)-2-butanol, acetate

A solution of 12.5 g of 4-[[3-(dimethylamino)propyl]thio]-1-(hexadecyloxy)-2-butanol, 73.9 g of acetic anhydride, and 29.3 g of triethylamine in 700 ml of chloroform was refluxed for 35 hours. Solvent and excess anhydride were removed at reduced pressure. TLC (silica gel, chloroform-methanol-water 70:30:5) indicated that some unreacted starting material remained; 40 ml of acetic anhydride and 0.2 g of sodium acetate were added and the mixture was refluxed for 15 minutes. The excess anhydride was removed at reduced pressure at 40°-60° C. The residue was dissolved in ether-methanol, treated with activated, charcoal and filtered through a pad of silica gel. Solvent was removed giving 13.2 g of product as a yellow oil.

EXAMPLE 65

3-[[3-(Acetyloxy)-4-(hexadecyloxy)-butyl]-thio]-N,N,N-trimethyl-1-propanaminium, Iodide A solution of 12.0 g of 4-[[3-dimethylamino)propyl]thio]-1-(hexadecyloxy)-2-butanol, acetate and 3.59 g of methyl iodide in 200 ml of ether was allowed to stand at room temperature for 5 days. Solid was collected and washed with ether giving 11.3 g of product as a colorless powder.

EXAMPLE 66

3-[[3-(Acetyloxy)-4-(hexadecyloxy)butyl]sulfonyl]-N,N,N-trimethyl-1-propanaminium chloride To a solution of 3.5 g of 3-[[3-(acetyloxy)-4-(hexadecyloxy)-butyl]thio]-N,N,N-trimethyl-1-propanaminium iodide in 150 ml of dichloromethane was added 9.0 g of 40% peracetic acid. After standing overnight, a saturated solution of sodium bisulfite was added until the iodine color disappeared. Solvent was removed. Ethanol and then dichloromethane were added and then evaporated to remove the last traces of water. The residue was mixed with dichloromethane and filtered. The solvent was removed from the filtrate and the residue was dissolved in 400 ml of dichloromethane-methanol (1:2). The solution was stirred with 100 g of chloride ion exchange resin (Bio-Rad AGI-X2) for 10 minutes. The mixture was filtered and the filtrate was stirred with another 50 g of resin. The mixture was filtered and solvent wa removed. The residue was triturated with ether and 2.65 g of product was collected as a white powder which did not have a well defined melting point.

Compounds of formula 44 are useful as antihypertensive agents. For example, in the antihypertension assay describe above, 3-[[3-(acetyloxy)-4-(hexadecyloxy)-butyl]sulfonyl]N,N,N-trimethyl-1-propanaminium chloride reduced the blood pressure in the spontaneously hypertensive rat 20 mm Hg at a dose of 10 mg/kg (iv).

What is claimed is:

1. A method of treating hypertension in a warm-blooded animal comprising administering to said animal an effective amount of a compound represented by the formula:

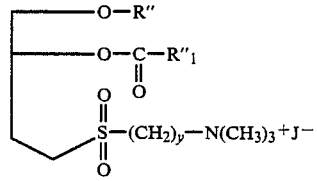

wherein
R'' is a $C_2$–$C_{20}$ alkyl group,
R''$_1$ is a $C_1$ to $C_4$ alkyl group,
y is an integer from 2 to 10, and
J is a pharmacologically acceptable anion.

2. A method as defined in claim 1 wherein said compound is a compound of the formula:

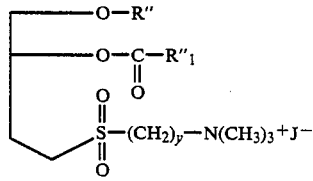

wherein
R'' is a $C_2$–$C_{20}$ alkyl group,
R''$_1$ is a $C_1$ to $C_4$ alkyl group,
y is an integer from 2 to 10, and
J is a pharmacologically acceptable anion, said compound being 3-((3-(acetyloxy)-4-hexadecyloxy)- butyl)-sulfonyl-N,N,N-trimethyl-1-propanaminium chloride..

3. A pharmaceutical composition in dosage unit form comprising a compound represented by the formula:

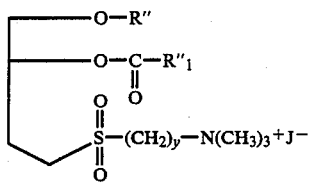

wherein R" is a $C_2$–$C_{20}$ alkyl group,
R"₁ is a $C_1$ to $C_4$ alkyl group,
y is an integer from 2 to 10, and
J is a pharmacologically acceptable anion in association with a pharmaceutically acceptable carrier.

4. A pharmaceutical composition as defined in claim 3 wherein said compound is a compound of the formula:

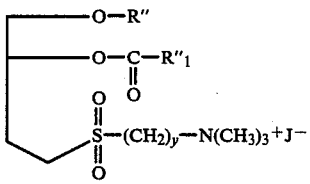

wherein
R" is a $C_2$–$C_{20}$ alkyl group,
R"₁ is a $C_1$ to $C_4$ alkyl group,
y is an integer from 2 to 10, and
J is a pharmacologically acceptable anion, said compound being 3-((3-(acetyloxy)-4-(hexadecycloxy)-butyl)-sulfonyl-N,N,N-trimethyl-1-propanaminium chloride.

5. A compound of the formula:

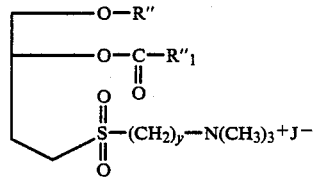

wherein
R" is a $C_2$–$C_{20}$ alkyl group,
R"₁ is a $C_1$ to $C_4$ alkyl group,
y is an integer from 2 to 10, and
J is a pharmacologically acceptable anion.

6. A compound of the formula:

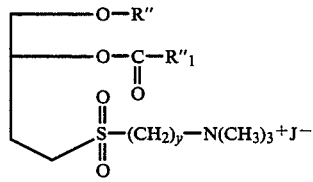

wherein
R" is a $C_2$–$C_{20}$ alkyl group,
R"₁ is a $C_1$ to $C_4$ alkyl group,
y is an integer from 2 to 10, and
J is a pharmacologically acceptable anion, said compound being 3-((3(acetyloxy)-4-(hexadecyloxy)-butyl)-sulfonyl)-N,N,N-trimethyl-1-propanaminium chloride.

* * * * *